United States Patent
Park

(10) Patent No.: US 10,933,154 B2
(45) Date of Patent: Mar. 2, 2021

(54) AROMA DIFFUSION MODULE AND AROMA DIFFUSION CONTAINER INCLUDING THE SAME

(71) Applicant: University-Industry Cooperation Group of Kyung Hee University, Yongin-si (KR)

(72) Inventor: Seung-Kook Park, Yongin-si (KR)

(73) Assignee: UNIVERSITY-INDUSTRY COOPERATION GROUP OF KYUNG HEE UNIVERSITY, Yongin-si (KR)

(*) Notice: Subject to any disclaimer, the term of this patent is extended or adjusted under 35 U.S.C. 154(b) by 177 days.

(21) Appl. No.: 16/091,921

(22) PCT Filed: May 26, 2017

(86) PCT No.: PCT/KR2017/005506
§ 371 (c)(1),
(2) Date: Oct. 5, 2018

(87) PCT Pub. No.: WO2017/204590
PCT Pub. Date: Nov. 30, 2017

(65) Prior Publication Data
US 2019/0111171 A1    Apr. 18, 2019

(30) Foreign Application Priority Data

May 27, 2016 (KR) .................. 10-2016-0065872

(51) Int. Cl.
*A61L 9/12* (2006.01)
*G09B 19/00* (2006.01)
(Continued)

(52) U.S. Cl.
CPC .............. *A61L 9/12* (2013.01); *A61B 5/4011* (2013.01); *A61L 9/01* (2013.01); *A61L 9/013* (2013.01);
(Continued)

(58) Field of Classification Search
None
See application file for complete search history.

(56) References Cited

U.S. PATENT DOCUMENTS 6,558,322 B1 * 5/2003 Busch ............... A61B 5/00
600/303
8,668,885 B2   3/2014 Wirz
(Continued)

FOREIGN PATENT DOCUMENTS

FR    2559931 A1 * 8/1985 ............ A61B 5/00
JP    2014211437 A * 11/2014 ............ B01L 3/523
(Continued)

OTHER PUBLICATIONS

Machine translation of FR 2559931 A1. Retrieved from EPO website on Jul. 27, 2020. (Year: 2020).*
(Continued)

*Primary Examiner* — Jennifer A Leung
(74) *Attorney, Agent, or Firm* — Seed Intellectual Property Law Group LLP

(57) ABSTRACT

Disclosed are an aroma diffusion module and an aroma diffusion container including the same. The aroma diffusion container according to an embodiment of the present invention includes a container body; an opening and closing unit coupled to the upper end of the container body; and an aroma diffusion module mounted in the container body, in which the aroma diffusion module includes a porous module body; a first hollow formed at one side of the module body; and a second hollow formed inside the module body, a
(Continued)

porous aroma diffusion medium is accommodated in the first hollow, and the second hollow allows external air to be introduced into the container body through a slit of a membrane member unit. According to the present invention, there is an advantage of providing various types of aroma diffusion kits which can be efficiently used to feel, distinguish, memorize, and express aromas of favorite beverages and food, such as wine, coffee, tea, beer, and whiskey in which the aroma is important, while maximizing the number of use times as well as being easy to use and enabling a long-term storage.

15 Claims, 8 Drawing Sheets

(51) Int. Cl.
    *A61L 9/013*     (2006.01)
    *A61L 9/01*     (2006.01)
    *A61B 5/00*     (2006.01)

(52) U.S. Cl.
    CPC ............... *A61L 9/125* (2013.01); *A61L 9/127* (2013.01); *G09B 19/00* (2013.01); *A61L 2209/13* (2013.01)

(56) References Cited

U.S. PATENT DOCUMENTS

| | | | |
|---|---|---|---|
| 2006/0046241 A1* | 3/2006 | Houri | ..................... A61L 9/042 434/365 |
| 2010/0184006 A1* | 7/2010 | Schmitt | .................. G09B 19/00 434/127 |
| 2017/0028091 A1* | 2/2017 | Desgagne | ............ B65D 81/266 |
| 2019/0008134 A1* | 1/2019 | Miyamoto | ............... C09K 3/00 |

FOREIGN PATENT DOCUMENTS

| | | |
|---|---|---|
| KR | 10-0801145 B1 | 1/2008 |
| KR | 10-2012-0109541 A | 10/2012 |
| KR | 10-2012-0118548 A | 10/2012 |
| KR | 10-2013-0041498 A | 4/2013 |
| KR | 10-20140024761 A | 3/2014 |
| KR | 10-1434266 B1 | 8/2014 |

OTHER PUBLICATIONS

Machine translation of JP 2014-211437A. Retrieved from JPO website on Jul. 27, 2020. (Year: 2020).*

* cited by examiner

AROMA DIFFUSION MODULE AND AROMA DIFFUSION CONTAINER INCLUDING THE SAME

TECHNICAL FIELD

The present invention relates to an aroma diffusion module and an aroma diffusion container including the same.

BACKGROUND ART

As a representative favorite drink for enjoying an aroma, wines, coffees, beers, sakes, teas (green tea, and fermentation tea) and the like are included.

In the case of wines, the kinds of aromas are very various depending on a variety, a cultivation area and a manufacturing method.

When a process of manufacturing the wines is briefly described, after harvested grapes are crushed and added with yeast, alcohol and aroma components are generated through a fermentation process. While the fermented wines are aged in a stainless steel tank or an oak barrel, the amount of coarse and nasty volatile components produced during the fermentation process is reduced and taste is improved.

The aroma component of the wine is generated by not only an inherent aroma component according to a type of raw grape but also the yeast used in fermentation.

In addition, when the wines are aged using the oak barrel after the fermentation, the aroma component on the inner surface of the oak barrel, such as vanilla, caramel, butter, coconut and the like, may be combined with the aroma of the wines to manufacture wines of higher quality.

The characteristics of such wines are mainly expressed by the aroma. For example, in the tasting note of the 2012 Napa Valley Franciscan Cabernet Sauvignon wine, the expression of "ripe plum, dark chocolate, baking spice, caramel, vanilla, blackberry, plum, cocoa, sage" is written.

As a tool used for expressing various aromas of the wines, there is a printed matter called "Aroma wheel". However, there are many difficulties in recognizing or expressing the characteristics of the actual aroma unless actual consumers directly smell the various aromas of the wines with nose and check the aromas.

This is because unlike vision or hearing, the aroma is difficult to remember because the aroma can not be seen or heard. Therefore, in order to recognize and express the aroma, it is necessary to smell the aroma of the wine and a reference aroma compound in alternating manner.

In particular, the process of distinguishing and memorizing the aromas using the reference aroma compound is very important not only for evaluating the quality of wines by a wine manufacturing company, but also for consumers who enjoy wines.

In addition, it is necessary to grasp favorite aroma characteristics of consumers in the importing countries for marketing when manufacturing wines or exporting wines. However, even though the expression is the same, it is impossible to accurately recognize or express the aromas due to a different expression even in the same type of aroma or differences from the food culture and the living environment even in the same expression.

Therefore, in order to accurately recognize and express the aroma of a complicated wine, it is necessary to repeat the process of memorizing and expressing the aroma of the complicated wine while comparing an aroma of the actual wine by using various reference aroma compounds as described above.

In addition, it is urgently required to develop a tool and a method for standardizing the aroma expression of favorite beverages commonly used in the world that are economically and culturally important (e.g. coffee, beer, sake, and tea, as well as wine).

For the above reasons, there has been conventionally provided a "wine aroma kit" in which various types of aromas that can be felt in the wine are contained in 10 to 90 small glass vials.

This "wine aroma kit" is sold to wine makers, wine sellers, wine specialists, wine lovers, wine education institutes, wine educators, wine dealers, wine marketers and consumers all over the world.

However, such a conventional wine aroma kit, that is, an aroma reference tool of wine, is provided in a state a liquid aroma of 3 to 5 mL is contained in a small glass vial (ca. 2×4 cm) and sealed with a screw cap.

Therefore, the conventional wine aroma kit is used by a method of opening the screw cap, dampening a liquid in a bottle on the paper using a thin and long paper called a "fragrance/perfume test strip" (hereinafter referred to as "aroma test paper") and smelling the aroma near the nose. At this time, since the user directly smells a high-concentration liquid aroma component with the nose, there is a large difference from the aroma of the actual wine.

In addition, since the strength of the aroma is too strong, after one type or two types of aromas smell, the olfactory cells of the nose are easily desensitized and thus it becomes impossible to evaluate subtle and weak aromas of the wine.

In addition, since various types of aroma vials are opened and the liquid aroma compound is absorbed on the aroma test paper and placed on a desk, it is very difficult to achieve the purpose of distinguishing the aromas of wine since various kinds of strong aromas are spread and mixed at the same time.

In addition, since most of the aroma components are contained in the vial in an essential oil state, the aroma components may be spilled or poured in the process of opening the screw cap, so that the surrounding area may be contaminated with strong aroma.

In addition, when the cap is loosened, the aroma component flows out into a gap between the cap and the container, the surrounding area may be contaminated with the aroma and when the cap is often opened, the aroma component is easily deformed by oxygen in the air.

Also, whenever a small amount (about 4 mL) of aroma liquid is used, the aroma liquid smears on the aroma test paper, so that the number of used times is small. For example, when 0.1 mL of the aroma liquid is soaked on paper once in use, the aroma liquid is used only 40 times.

In addition, when the aroma of the wine smells, a strong volatile alcohol smell is inevitably taken at the same time, and the conventional wine aroma kit can not reproduce the alcoholic smell of the wine, so it may be different from the characteristics of the actual aroma.

In addition to wine, coffee is an aroma important food. There is a big difference in the aroma characteristics of coffee depending on a kind of wine, a cultivation area, a processing method of green beans, a roasting method, and an extraction method.

In recent years, the demand for coffee has increased rapidly around the world, and the quality of the coffee has improved and the price has surged. Accordingly, consumers are increasingly interested in the aroma of coffee itself.

In the Specialty Coffee Association of America, the "coffee flavor wheel" has long been used as a tool to distinguish and express 36 kinds of coffee aromas. This tool is used in various fields such as coffee makers, coffee education institutions, coffee shop staffs, marketing, consumers, and the like.

Specially, as the quality of coffee has recently become higher, the aroma of coffee is represented on the coffee wrapping paper in the same manner as the expression of the aroma of wine. For example, in Ethiopian Yirgacheffe coffee, terms of lavender, lilac, honey suckle, sweet citrus, fresh-cut cedar, red berries, strawberry, raisin, cherry juice, lychee, papaya and cacao have been used as the aroma expression.

However, as in the case of wine, it is very difficult to recognize and express the aroma of coffee.

In addition to wine and coffee, as favorite beverages for the aroma, beer (especially, craft beer), sake, tea, whiskey, and the like are included. In the past, these beverages were merely drinking beverages.

However, in recent years, the aroma characteristics play an important role in determining the satisfaction and price of consumers. Accordingly, the manufacturer or the sales company displays the aroma characteristics of the product on a label or uses the aroma characteristics for marketing. For example, in the case of craft beer, a liquid "aroma kit" such as wine is used to distinguish and express the aroma.

There is also a product called "FlavorActiV" which is manufactured by absorbing various kinds of aroma components into sugar and β-cyclodextrin and then putting it into a pill-type gelatin capsule.

However, the "FlavorActiV" diffuses the aroma by directly putting and dissolving the to capsule in the beer. Therefore, there are disadvantages that since the "FlavorActiV" is used once by preparing a plurality of glasses for each use by the user, pouring the beer into each of the glasses, and adding and dissolving the capsule containing different kinds of aroma components, it is difficult to use the "FlavorActiV" except for a laboratory or a kitchen.

In addition, the intensity of the aroma cannot be adjusted, and it is very inconvenient to use itself.

In addition, the aroma is often generated through a chemical reaction (for example, acetaldehyde), and in some cases, the capsule and the component (β-cyclodextrin) contained in the capsule are coupled to the aroma component of the original beer aroma to reduce the volatility.

In addition, the partially dissolved capsule remains in the cup, which is visually very uncomfortable, and may be harmful to the human body in the case of drinking with the beer contained in the beer glass.

Other standard beer aroma kits which are commercially available include a Siebel Institute Sensory Training kit. In the kit, each of 1 mL of 44 liquid aromas is accommodated in a glass ampoule, and the top of the glass ampoule is broken and opened in use, and then the aroma liquid in the glass ampoule is poured and used into the beer.

This kit is a disposable, and there is a problem in that small pieces of glass generated when breaking the top of the glass ampoule may be mixed with the beer and may be harmful to the human body by putting a chemically synthesized substance directly into the beer to take a smell or drink with the beer.

Accordingly, it is required to develop effective and safe standard aroma diffusion tools which can easily recognize the aroma characteristics in favorite beverages such as beer, sake, tea, whiskey, etc., which are important in aroma like wine and coffee.

The problems of the above-described prior art are summarized as follows.

Liquid aroma kits which are currently sold and used on the market are sold by putting to about 4 mL of various types of liquid aromas that constitute wine, coffee, tea, beer, and whiskey in a small glass vial.

Such a conventional method of using a liquid aroma kit is a method of holding a vial with one hand and turning and opening and closing a screw cap with the other hand, and thus it is disadvantageous in that it is very inconvenient in used.

In addition, when using a conventional liquid aroma kit, it is necessary to use an elongated aroma test paper to absorb a liquid aroma material and then to bring the liquid into the nose and take a liquid smell. Therefore, there is a problem that the high-strength liquid aroma at a high concentration desensitize the olfactory nerve cells of the nose and as a result, it is very difficult to distinguish the aromas.

In addition, the conventional liquid aromatic kits are very strong in the aroma intensity, and are exposed to the air whenever used, and diffused therearound. Accordingly, since various kinds of aromas may be mixed with each other in the same space, there is a limit in that itis difficult to perform accurate evaluation of the aroma.

In addition, since the conventional liquid aromatic kits are used by absorbing the liquid aroma material into paper, there has been a limit in that it is difficult to adjust the aroma intensity.

In addition, the conventional liquid aromatic kits are in a liquid state, and have a disadvantage in that the conventional liquid aromatic kits are often exposed to the air during use and are likely to be deteriorated by oxygen in the air.

In addition, the conventional liquid aromatic kits have a small number of times of use because the liquid aroma is absorbed and used in the aroma test paper and then the aroma test paper is not reused and immediately discarded. For example, in the case of a 4 mL liquid aromatic kit, there was a limit in that only 0.1 mL was applied to paper at one time and only 40 times were used when used. Furthermore, it was inevitable that the room was contaminated with a strong aroma due to the discarded aroma test paper.

Specifically, in the case of the wine, alcohol smell is an important component of the wine and has a great influence on the characteristics of aroma. Nevertheless, the conventional wine aroma kit has a problem that it is difficult to express the actual wine aroma because it is impossible to reproduce the wine aroma.

In addition, since the conventional liquid aroma kit has a screw cap made of a plastic material, the shrinkage and swelling may be repeated according to the temperature change. Therefore, even if the screw cap is completely turned and blocked, there is a fatal problem in that a liquid material at a high concentration is leaked out, or the air continuously flows from the outside, and thus the deterioration due to oxidation easily occurs.

In addition, the conventional aroma kit has the limitation that blind people can not use the aroma kit because the liquid aroma component in the small vial is wetted on the aroma test paper.

On the other hand, the aroma contributes greatly to the therapeutic effects such as improvement of cognitive ability and concentration, and mind and body stability.

A convenient, safe and effective tool to easily recognize and remember the aroma may be used not only in the field of food, but also in improving the cognitive abilities of early childhood education. In other words, infants and young children take a variety of dishes, food, flowers, trees and surrounding smells during their growth to greatly contribute to the improvement of intelligence development and creative thinking as well as cognitive ability.

Therefore, books and videos made with pictures and photographs that can recognize and memorize various kinds of aromas that can be seen and felt around the life together with the aroma diffusion tool are a great help to raise the creativity by improving the emotion and intelligence of infants and young children.

In addition, the aroma diffusion tool may be effectively used as an alternative therapy for early diagnosis and prevention of deterioration of memory or brain function due to aging and dementia and Parkinson's disease, which are serious diseases related to brain function. In particular, it is reported on the research that labender, lemon balm, peppermint, bergamot, and rosemary can not only diagnose brain cognitive function but also activate related cells to improve memory function.

Accordingly, a proposal of a new technique for solving the problems of the conventional aroma related technology as described above is urgently required.

(Patent Document 1) KR2014-0024761 A1
(Patent Document 2) KR2012-0109541 A

DISCLOSURE

Technical Problem

Therefore, the present invention has been made in order to overcome the problems of the prior art described above, and an object of the present invention is to provide an aroma diffusion container including an aroma diffusion module in which due to ease of use and a long-term storage, a user can recognize each aroma and easily express characteristics of the aromas by distinguishing various and complicated types of aromas which can be felt in favorite food or beverages, that is, coffee, wine, tea, beer, whiskey, etc., in which the aroma is important, as individual aroma components.

Technical Solution

In order to accomplish the above object, the present invention provides an aroma diffusion container comprising: a container body; an opening and closing unit coupled to the upper end of the container body; and an aroma diffusion module mounted in the container body, in which the aroma diffusion module includes a porous module body; a first hollow formed at one side of the module body; and a second hollow formed inside the module body, a porous aroma diffusion medium is accommodated in the first hollow, and the second hollow allows external air to be introduced into the container body through a slit of a membrane member unit.

The first hollow may be in contact with the inner side of a bottom portion of the container body, and the second hollow may be in close contact with a head portion formed on the upper end of the container body.

The aroma diffusion module may have a column shape extending from the head portion of the container body to the bottom portion of the container body.

The container body may be made of a flexible material such as LDPE or HDPE.

The container body may have a multilayered structure in which a nylon layer is formed between resin layers formed of the flexible material.

An antioxidant and a deoxidizer may be contained in the porous aroma diffusion module.

The antioxidant may include at least one of butylated hydroxy aisole (BHA), butylated hydroxy toluene (BHT), TBHQ, EDTA, phenolic acids, and polyphenols.

The opening and closing unit may include a valve member having the membrane member made of the flexible material, and the membrane member may be convexed upward.

The opening and closing unit may include a sniffing port which is coupled to the container body and gradually expanded upward.

The present invention provides an aroma diffusion kit comprising at least one or more of multiple aroma diffusion containers, in which aroma diffusion media of the multiple aroma diffusion containers include different types of aroma materials.

The porous aroma diffusion medium absorbing a liquid aroma component may be provided in the container body.

In the sealed container body, an aroma component volatilized to a gaseous state from the liquid aroma component absorbed in the porous aroma diffusion medium may be present at a predetermined concentration.

Ethanol may be injected into the second hollow through the slit of the membrane member unit by a pipette.

The airtightness of the aroma component in the gaseous state present inside the container body may be maintained by a multiple sealed structure formed by an edge of the one-touch cap, a protrusion formed on the inner surface of the one-touch cap, the membrane member, and the like.

The aroma component in the gaseous state present inside the container body may be discharged to the outside through the sniffing port by opening the one-touch cap and pressing the container body, and the pressure inside the container body may be maintained in an initial state before the aroma is discharged by the air introduced by passing through the porous module body from the outside after the aroma is discharged, and oxygen in the air introduced at this time may be removed by the deoxidizer and the antioxidant contained in the porous aroma diffusion module.

Advantageous Effects

The present invention has the following effects.

First, the aroma diffusion medium is inserted into the first hollow to diffuse a certain concentration of aroma, so that an aroma at a desired concentration may be maintained.

Second, the diameter of the sniffing port increases in upward direction. That is, the sniffing port serves to effectively transfer the aroma gas diffused through the valve unit to the olfactory cells of the nose. Thus, diffusion of the aroma or mixing with the surrounding odor is minimized. In other words, the sniffing port 220 may limit the diffusion region of the aroma particle to a specific region. Therefore, since while aroma particles are discharged to another space and not mixed with other aromas, only the aroma desired by the user is transferred to the olfactory cells of the nose, so that the user may effectively distinguish the aroma.

Third, the aroma component stored in the container body may be smelt by freely controlling a required volume by one hand. That is, the aroma component is vaporized from the aroma absorbed in the aroma diffusion medium, diluted to a certain concentration in the container body, and stored in the container body. Accordingly, since the user does not smell the aroma component directly from the liquid, the desensitization of the olfactory cells is prevented, and the user can use the aroma component by diffusing the aroma similar to the aroma existing in the actual wine or coffee. Therefore, there is an advantage that more accurate aroma recognition becomes possible.

Fourth, the container body may be formed of a resilient material, and the opening and closing unit provided at an inlet (outlet) of the container body may be opened and closed at one-touch. Accordingly, there is an advantage in that the user may press the container body with user's fingers to adjust the pressure inside the container body, thereby adjusting and using the amount of the aroma to a required amount.

Fifth, the base portion has a circular ring shape and extends upward by surrounding the edge of the membrane member. Therefore, when pressure is generated by pressing the container body with the fingers, the aroma particles diffused through the slit may be uniformly guided in the vertical upward direction, so that more accurate aroma recognition becomes possible.

Sixth, the aroma diffusion module contains an antioxidant (not illustrated) and a deoxidizer (not illustrated). Thus, by removing oxygen in the air introduced into the container body, oxidation of the whole aroma particles inside the container body is prevented. Therefore, there is a strong point that it is possible to use the original aroma characteristic while preserving for a long time.

Seventh, long-term use is possible. Conventional liquid aroma kits are used by repeated opening and closing the vials so that the loss of aroma is large. Therefore, when the period of use is about 3 years, the original aroma characteristics are significantly changed by the oxidation reaction and the chemical reaction, and thus, the performance is greatly deteriorated. In contrast, according to the embodiments of the present invention, use for up to five years is possible.

Eighth, there is an effect of increasing the number of use. In other words, since the aroma component of the liquid is gasified as necessary, the aroma component can be used at least 300 times.

Ninth, a small amount of alcohol may be injected into the container body without separating the opening and closing unit itself from the container body. In other words, the same state as when alcoholic beverages containing alcohol, such as actual wine, beer, or whiskey, may be prepared. Therefore, there is an advantage that it is possible to accurately distinguish and evaluate the aroma of these alcoholic beverages.

Tenth, a silicon-made valve unit (membrane valve) is installed in the opening and closing unit and an inlet of the valve unit is double-sealed by the one-touch cap. Furthermore, finally, the opening and closing unit has a triple-sealed structure in which the edge portion of the one-touch cap seals the upper portion of the ejection port of the container body. Accordingly, aroma components inside the container body are not discharged to the outside, or external air is not introduced into the container body.

Eleventh, braille display is possible because there is a sufficient space outside the aroma diffusion container. Therefore, the blind people can conveniently distinguish and use the aroma.

BRIEF DESCRIPTION OF DRAWINGS

The following drawings are merely basic examples for explaining the present invention in detail, and it is possible to design and manufacture various types of aroma containers based on the drawings.

MODE FOR INVENTION

Figure 1:
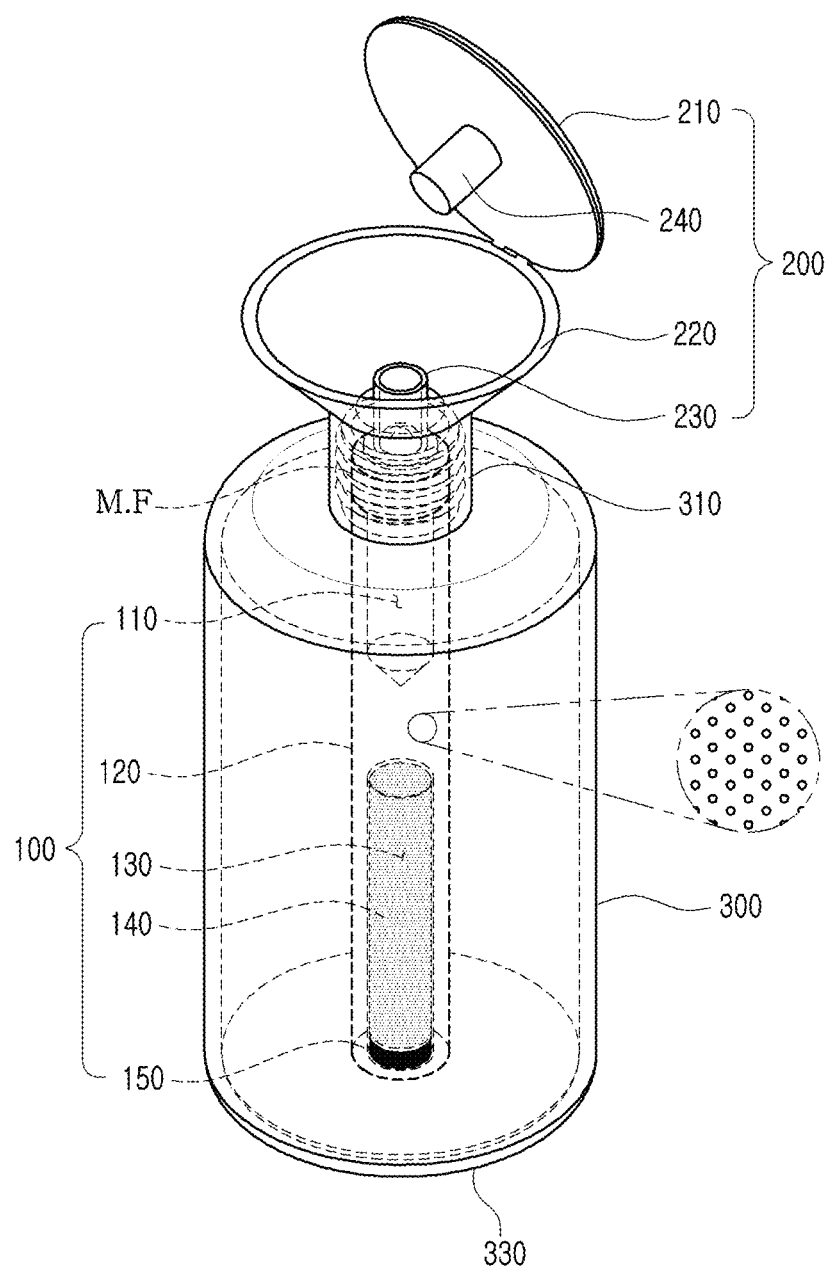
FIG. 1 is a whole projection perspective view according to a first embodiment of the present invention.

Hereinafter, the present invention will be described in detail with reference to the accompanying drawings.

In this process, the thicknesses of the lines and the sizes of the components shown in the drawings may be exaggerated for clarity and convenience of explanation. In addition, the terms to be described below are defined in consideration of the functions of the present invention, which may vary depending on the intention or custom of the user or the operator. Therefore, the definitions of these terms should be described based on the contents throughout this specification.

Referring to FIG. 1, the aroma diffusion container according to the first embodiment of the present invention includes a container body 300, an aroma diffusion module 100 installed in the container body 300, and an opening and closing unit 200 installed in the container body 300 to diffuse the aroma from the aroma diffusion module.

The aroma diffusion module 100 has a structure which is made of porous plastics and enables movement of aroma particles.

The entire aroma diffusion module 100 has a long column shape. A second hollow 110 is formed on one side of the aroma diffusion module 100 and a first hollow 130 is formed on the other side thereof.

The second hollow 110 is a groove which is long-recessed in a central axis direction of the aroma diffusion module 100 from the upper end of the aroma diffusion module 100.

In the first embodiment, the second hollow 110 has a hollow circular column shape, but is not limited thereto, and the lower end of the second hollow 100 may have a pointed conical shape in downward direction.

The first hollow 130 is a groove which is long-recessed in a central axis direction of the aroma diffusion module 100 from the lower end of the aroma diffusion module 100.

An aroma diffusion medium 140 containing aroma particles is inserted into the first hollow 130.

A plug-shaped locking device (not illustrated) may be provided at the lower end of the first hollow 130 to prevent the aroma diffusion medium 140 from being removed downward after the aroma diffusion medium 140 to be described below is inserted.

The second hollow 110 and the first hollow 130 are not connected to each other. In other words, the aroma diffusion module 100 has a structure in which the second hollow 110 is formed at an upper portion from the module body 120, and the first hollow 130 is formed at a lower portion from the module body 120.

In the first embodiment, the diameter of the second hollow 110 and the diameter of the first hollow 130 are the same as each other. Alternatively, the diameter of the second hollow 110 and the diameter of the first hollow 130 may be different from each other.

In the first embodiment, the aroma diffusion module 100 is in contact with the inner surface of a bottom portion 330 of the container body 300. Alternatively, the aroma diffusion module 100 may be spaced apart from the bottom of the container body 300 by a predetermined distance.

The aroma diffusion module 100 may be formed of a porous material.

The aroma diffusion module 100 contains an antioxidant and a deoxidizer. That is, the aroma diffusion medium 140 is located in a closed space inside the aroma diffusion module 100 containing the antioxidant and the deoxidizer. Therefore, deformation of the aroma absorbed in the aroma diffusion medium 140 is effectively prevented, so that the aroma diffusion medium 140 can be used for a long period of time.

The aroma diffusion medium 140 contains aroma particles in which a reference aroma compound in a liquid state is absorbed to be diffused from the aroma diffusion container according to various embodiments of the present invention. The aroma particles contained in the aroma diffusion medium 140 are uniformly distributed inside the container body 300 through the aroma diffusion module 100.

The aroma diffusion medium 140 may be formed of a porous material.

More particularly, about 0.5 mL to 1 mL of each reference aroma compound to be described below is absorbed in the aroma diffusion medium 140. The aroma diffusion medium 140 in which the reference aroma compound is absorbed is inserted into the first hollow 130 of the aroma diffusion module 100 formed of a porous plastic column (PPC).

At this time, the lower end of the aroma diffusion module 100 is closed and fixed with a cap (not illustrated) and then pushed into the bottom portion 330 of the container body 300 through an ejection port of the container body 300, so that the aroma diffusion module 100 is inserted into the container body 300.

The opening and closing unit 200 is formed in a sniffing port shape and includes a sniffing port 220 provided with a valve unit 230 and a one-touch cap 210 opening and closing the sniffing port 220.

At least one slit 235 is formed in the valve unit 230 so that the effusion of the aroma particles may be interrupted.

The one-touch cap 210 serves to open or close the sniffing port 220. A protrusion 240 formed on the inner surface of the one-touch cap 210 is inserted into an inner portion 231 of the base portion of the valve unit to prevent the aroma particles from being effused without notice.

The one-touch cap 210 is preferably opened and closed in a one-touch manner.

The sniffing port 220 limits a diffusion path of the aroma particles diffused from the valve unit 230. The sniffing port 220 has a structure in which the diameter of a horizontal section is gradually increased toward an upward direction.

Accordingly, the aroma particles diffused from the inner space of the sniffing port 220 through the valve unit 230 are naturally diffused to the surroundings and are effectively transferred to the olfactory tissue of the nose at the same time.

The valve unit 230 serves to diffuse the aroma particles evenly distributed inside the container body 300 to the outside of the container body 300. The valve unit 230 is provided at a position where the opening and closing unit 200 is fixed to the container body 300.

In the first embodiment, the valve unit 230 is provided with a membrane valve made of a flexible silicon material. Accordingly, the valve unit 230 may be operated very flexibly so as to quickly interrupt the aroma particles spreading inside the container body 300. Alternatively, the valve unit 230 may be formed of a different flexible material.

Figure 2:
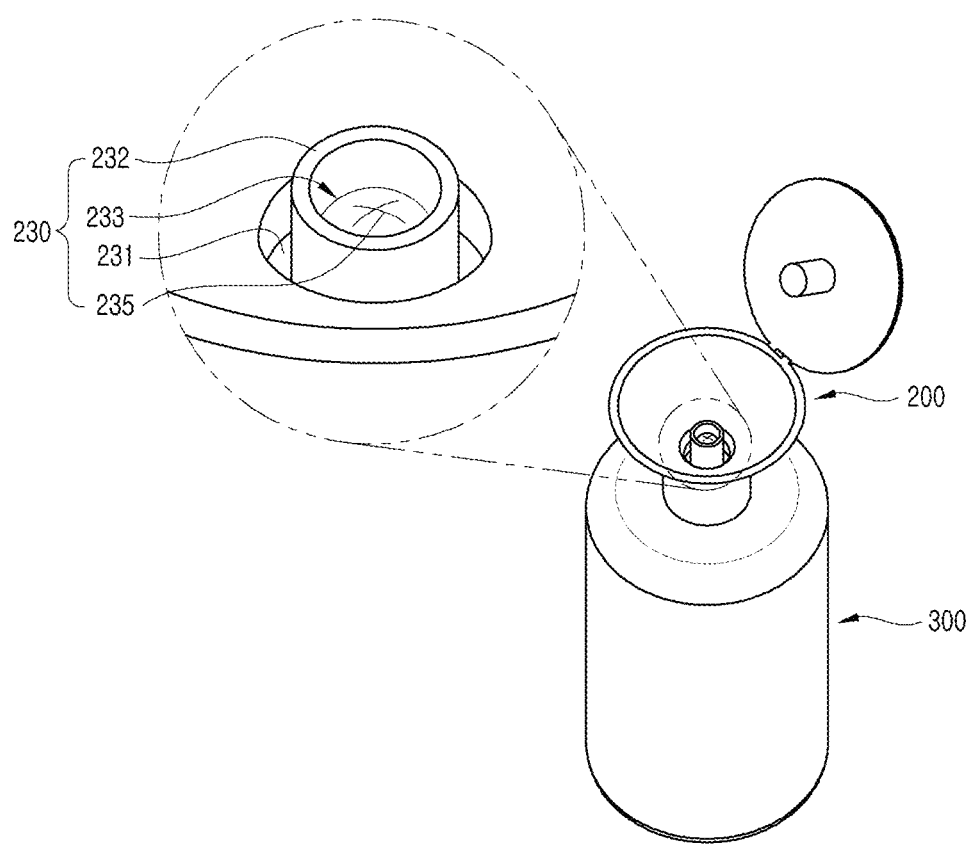
FIG. 2 is an upper side view according to the first embodiment of the present invention.

Referring to FIG. 2, the valve unit 230 includes a base portion 231, a membrane member 233, and a slit 235.

The base portion 231 has a circular ring shape and extends in an upward direction while covering the edge of the membrane member 233. The upper end of the base portion 231 is formed at a position higher than the upper end of the membrane member 233.

The membrane member 233 is formed to be convex upward as a whole. Alternatively, the membrane member 233 may be a flat structure (not illustrated).

The slit 235 is a portion where the aroma particles in the container body 300 are diffused when the container body 300 is pressurized. At least one slit 235 is formed in the membrane member 233 so that the effusion of the aroma particles may be interrupted.

As described above, since the base portion 231 has the circular ring shape and extends in the upward direction while covering the edge of the membrane member 233, the aroma particles diffused through the slit 235 may be uniformly guided in a vertical upward direction. In other words, the base portion 231 serves to guide the aroma particles diffused through the slit 235.

The airtightness of the aroma component in a gas state existing inside the container body 300 is maintained by a multiple sealed structure formed by an edge of the one-touch cap 210, a protrusion 240 formed on the inner surface of the one-touch cap 210, the membrane member 233, and the like.

The container body 300 may be formed to have a volume of about 30 mL to 120 mL. Preferably, the volume of the container body 300 may be formed in a volume of about 50 mL to 60 mL. This is because the volume is appropriate for the user to smell the aroma by pressing the container body 300 with one hand.

Figure 3:
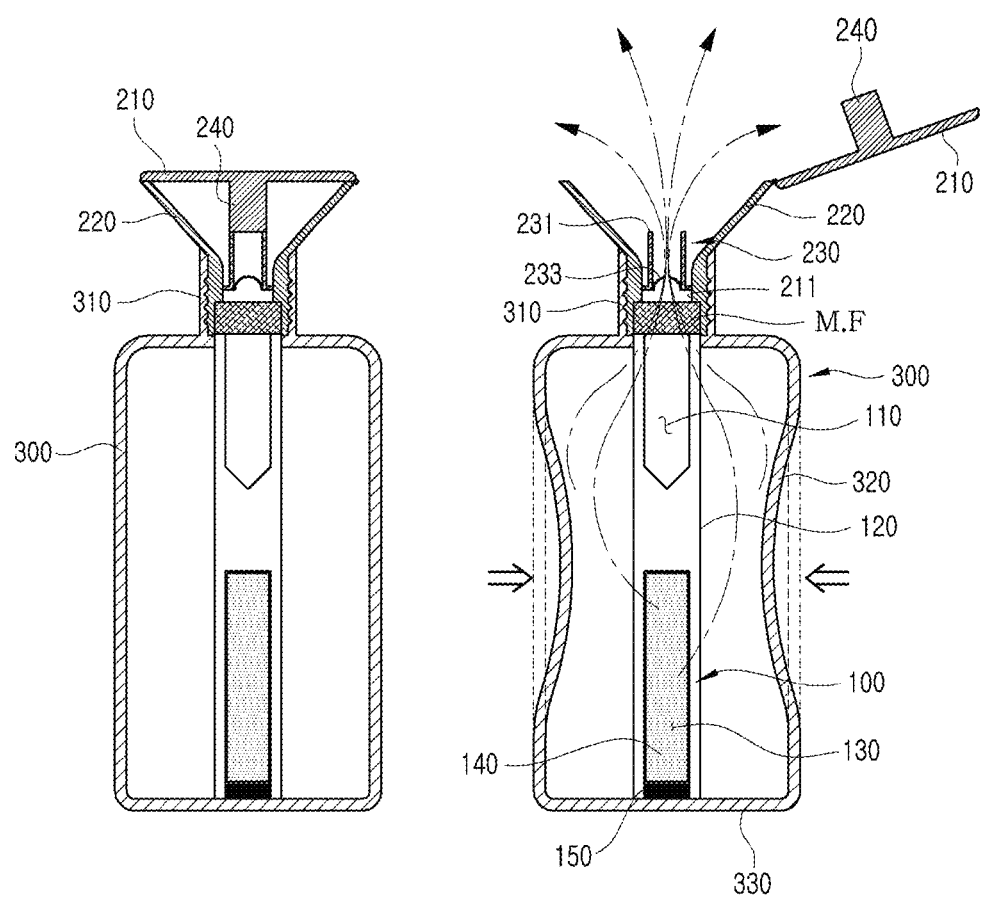
FIG. 3 is a view illustrating a first operation according to the first embodiment of the present invention.

Referring to FIG. 3, a process and an operation of diffusing the aroma of the aroma diffusion container according to the first embodiment of the present invention will be described.

First, the process of preparing the aroma diffusion container will be described.

First, about 0.5 mL to 1 mL of each reference aroma compound to be described below is taken to be absorbed in the aroma diffusion medium 140. Next, the aroma diffusion medium 140 containing the aroma particles absorbed with the reference aroma compound is installed in the aroma diffusion module 100. More specifically, the aroma diffusion medium 140 is inserted into the first hollow 130 of the porous aroma diffusion module 100.

The aroma diffusion module 100 with the aroma diffusion medium 140 inserted therein is inserted into the container body 300 through an ejection port formed in a head portion 310 of the container body 300.

At this time, the upper portion of the aroma diffusion module 100 is in close contact with the inner circumferential surface of the ejection port formed in the head portion 310 of the container body 300 and the lower portion thereof is tightly fixed to the bottom portion 330 of the container body 300.

Next, the valve unit 230 is tightly fixed to a connection portion 211 formed in the opening and closing unit 200.

In the opening and closing unit 200 provided with the valve unit 230, the outer circumferential surface of the connection portion 211 is in close contact with the head portion 310.

In the state where the one-touch cap 210 closes the sniffing port 220, the air and the aroma particles inside the container body 300 form an equilibrium state. That is, the aroma particles are evenly and uniformly diffused into the container body 300 from the aroma diffusion medium 140, resulting in completing preparation for diffusion to the outside of the container body 300.

Next, a process in which the aroma is diffused from the aroma diffusion container prepared through the above-described process will be described.

The user opens the one-touch cap 210 with one finger in one touch and presses a body portion 320 of the container body 300.

Since the container body 300 may be formed of a flexible material, the shape of the body portion 320 may be deformed toward the center of the container body 300 when the body portion 320 is pressed. More specifically, the container body 300 may be made of low density polyethylene (LDPE) or high density polyethylene (HDPE).

Further, the container body 300 may have a multi-layer structure. More specifically, a nylon layer is formed between resin layers formed of a flexible material such as the LDPE or HDPE. Accordingly, the aroma gas diffused from the aroma diffusion module 100 accommodated in the container body 300 is not effused to the outside without the user's operation.

When the body portion 320 is pressed, the pressure inside the container body 300 is increased to open the valve unit 230 so that the air inside the container body 300 is diffused to the outside of the container body 300. When the valve unit 230 is opened, the aroma particles uniformly diffused in the container body 300 are diffused to the outside through the slit 235 formed in the membrane member 233.

At this time, the aroma particles of the aroma diffusion medium 140 are also discharged from the aroma diffusion module 100, pass through the interior space of the container body 300, and are discharged from the slit 235 formed on the membrane member 233 through the second hollow 110 of the aroma diffusion module 100.

The aroma particles diffused to the outside are guided by the base portion 231 and the extension portion 232 of the base portion 231 and are raised uniformly in the vertical upward direction. Then, the aroma particles are effectively transmitted to the olfactory organ of the user's nose by the sniffing port 220, so that the user senses the aroma.

In addition, since the aroma particles diffused through the valve unit 230 may stay in the sniffing port 220, the aroma is not effused to another space, so that the user may very easily smell the aroma.

In other words, since the sniffing port 220 limits a diffusion region of the aroma particles to a specific region, the aroma particles are effused to another space and are not mixed with another aroma. Accordingly, only the aroma particles discharged through the valve unit 230 are transmitted to the olfactory organ, so that the user may effectively distinguish the aroma.

Figure 4:
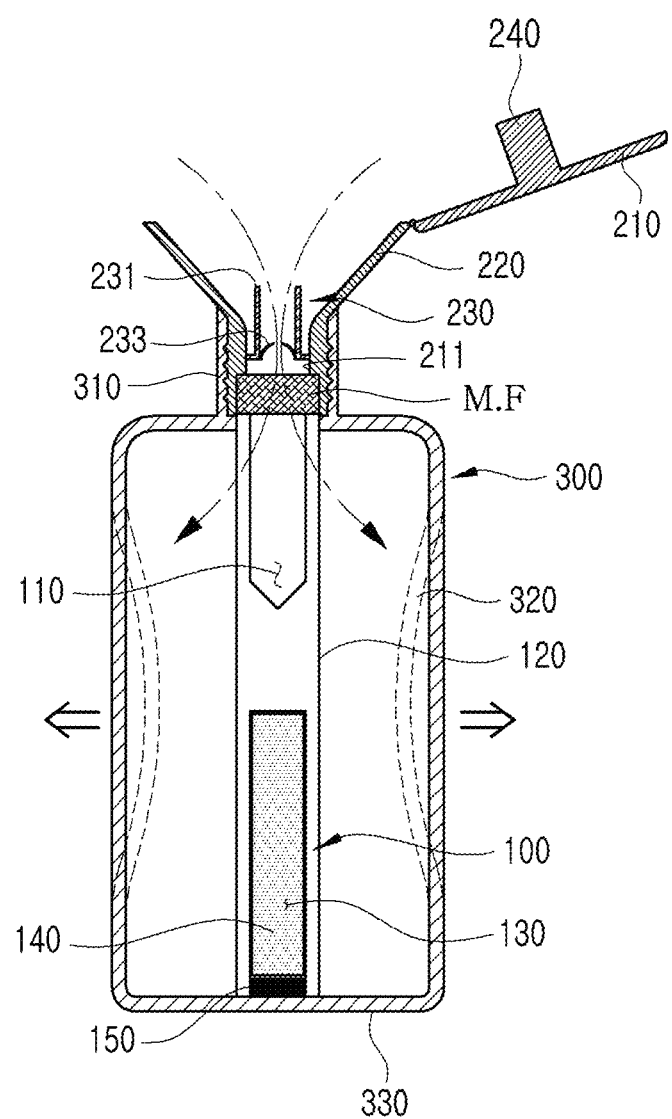
FIG. 4 is a view illustrating a second operation according to the first embodiment of the present invention.

A second operation according to the first embodiment of the present invention will be described with reference to FIG. 4.

When the force for pressing the container body 300 is removed, the container body 300 is restored to its original state.

At this time, since the pressure inside the container body 300 is reduced and the volume is expanded, the external air is introduced into the container body 300 through the slit 235 formed in the membrane member 233. Accordingly, the pressure inside the container body 300 is maintained in an initial state before the aroma is discharged by passing through the porous module body 120 by the air introduced from the outside after the aroma is discharged, and oxygen in the air introduced at this time is removed by the deoxidizer and the antioxidant contained in the aroma diffusion module 100.

When the external air is introduced into the container body 300, the external air is necessarily introduced through the aroma diffusion module 100.

More specifically, the external air is introduced into the interior space of the container body 300 through the second hollow 110 of the aroma diffusion module 100.

At this time, since the antioxidant and the deoxidizer (not illustrated) are contained in the aroma diffusion module 100, oxygen in the introduced air is removed.

The antioxidant may include at least one or one or more of butylated hydroxy aisole (BHA), butylated hydroxy toluene (BHT), tert-butylhydroxyquinone (TBHQ), ethylenediaminetetraacetic acid (EDTA), polyphenols, and phenolic acids (PG, OG).

Accordingly, oxidation of the whole aroma particles inside the container body 300 in which the aroma particles contained in the aroma diffusion medium 140 inside the container body 300 and the air introduced into the container body 300 are mixed is prevented. As a result, it is possible to use the aroma particles while maintaining an original aroma property for a long period of time.

In addition, fresh air introduced into the container body 300 and aroma particles contained in the aroma diffusion medium 140 are evenly mixed to maintain equilibrium between the air and the aroma particles.

Finally, the one-touch cap 210 is closed to store the aroma particles.

Figure 5:
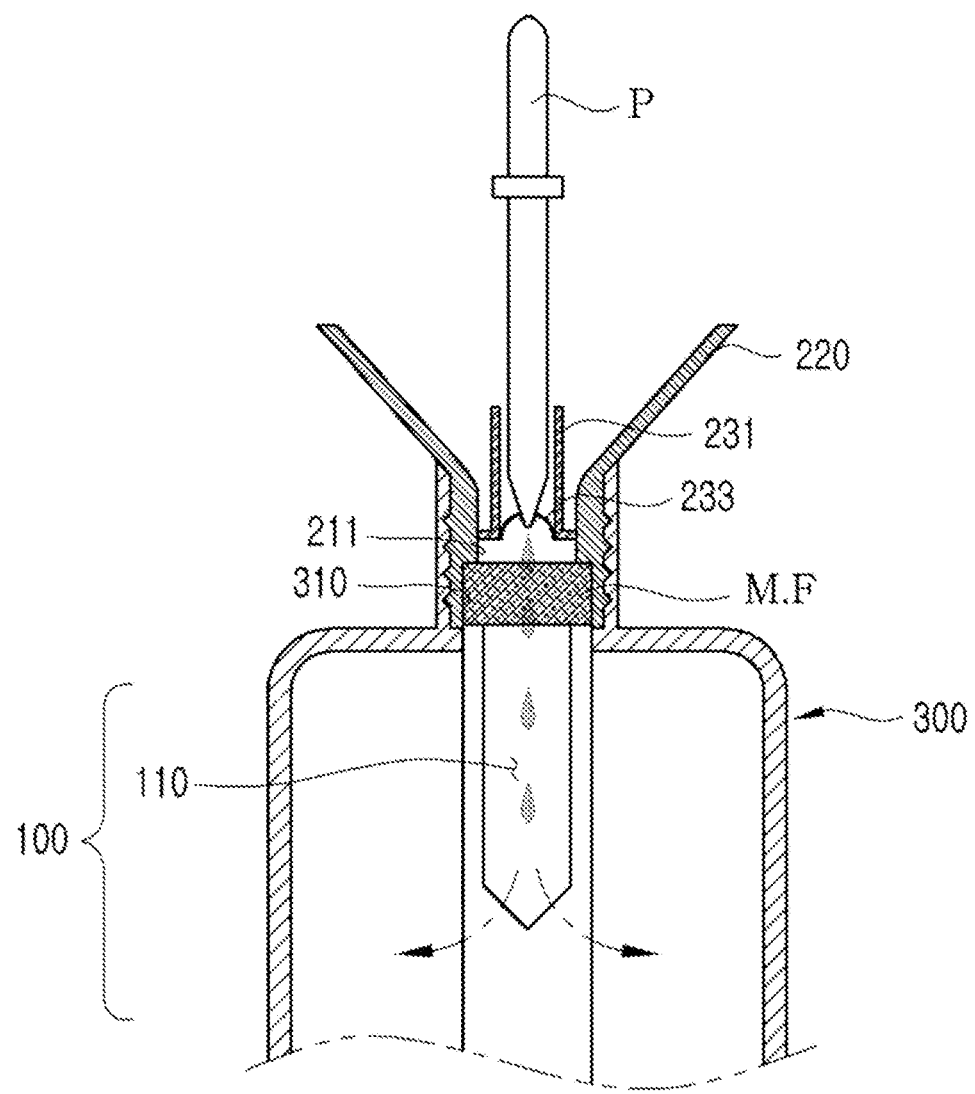
FIG. 5 is a view illustrating an alcohol injection process according to the first embodiment of the present invention.

An alcohol injection process according to the first embodiment of the present invention will be described with reference to FIG. 5, in order to diffuse the aromas of alcoholic beverages such as wine. Examples of the alcohol to be injected at this time may include ethanol and the like.

The alcohol is injected into the container body 300 by inserting a pipette P through the membrane member 233 according to the first embodiment described above.

The injected alcohol is primarily accommodated into the second hollow 110 formed in the aroma diffusion module 100 and the alcohol is diffused into the inner space of the container body 300 through the aroma diffusion module 100 because the alcohol is a volatile substance.

Accordingly, the injected alcohol is spread evenly inside the container body 300 together with the aroma particles diffused into the container body 300.

The second hollow 110 has a shape in which the diameter of the cross section is gradually reduced downward. Accordingly, the impact applied to the alcohol initially injected into the second hollow 110 is alleviated, and thus more stable injection is possible. In this case, it is preferable to inject an amount of the injected alcohol to correspond to the actual alcohol content of the alcoholic beverages.

Specially, in the case of wine, since it is possible to diffuse the respective aromas suitable for various kinds of wines as they are, it is possible to produce a more realistic aroma of the alcoholic beverages.

Figure 6:
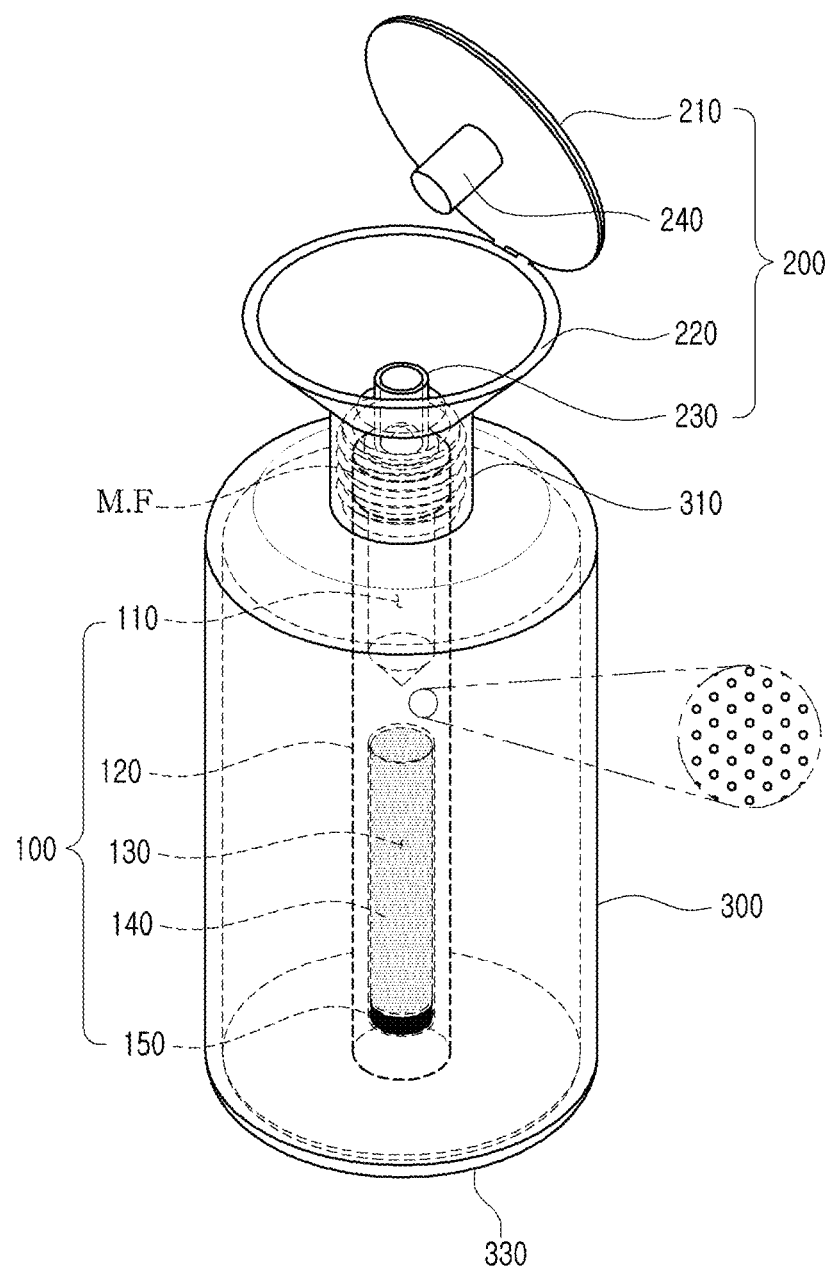
FIG. 6 is a whole projection perspective view according to a second embodiment of the present invention.

A second embodiment of the present invention will be described with reference to FIG. 6.

The upper portion of the aroma diffusion module 100 may be in close contact with the inner circumferential surface of the ejection port and the lower portion may be spaced apart from the bottom portion 330 of the container body 300 to be fixed.

Figure 7:
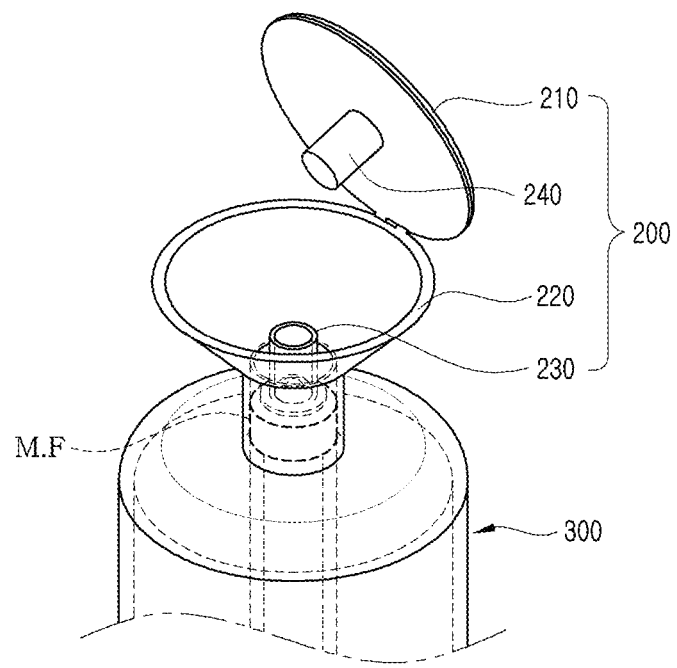
FIG. 7 is a partial perspective view according to a third embodiment of the present invention.

Referring to FIG. 7, the opening and closing unit 200 and the container body 300 may be integrally formed.

Further, the aroma diffusion container of the present invention may be formed in a character shape according to the taste of the user. In particular, the opening and closing unit 200 may be formed in a shape of a head portion of the character, and a mouth portion of the character may perform the role of the one-touch cap 210.

Even when the aroma diffusion container is formed in a character shape, the above-described aroma diffusion module 100 is accommodated in the container body 300. Further, the opening and closing unit 200 formed in the shape of the head portion of the character may perform the same function as the opening and closing unit 200 of the above-described embodiments.

Figure 8:
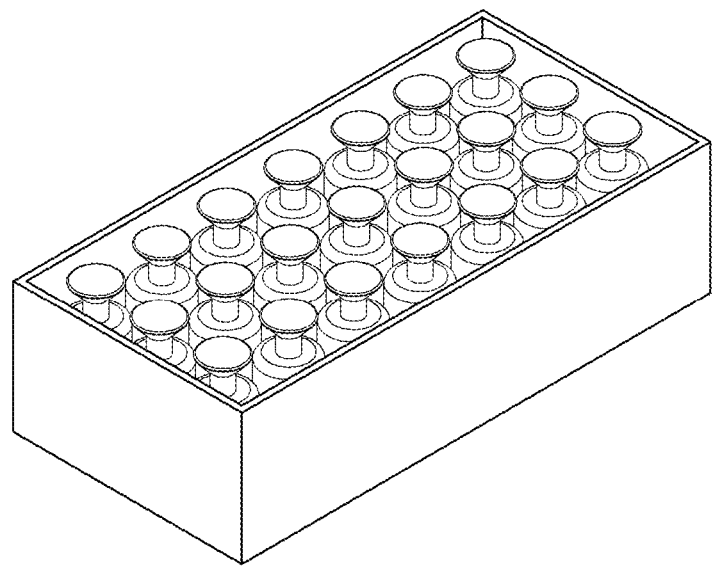
FIG. 8 is a perspective view of a plurality of aroma diffusion containers which are box-packaged according to the first to third embodiments of the present invention.

Further, a kit may be configured by manufacturing a plurality of aroma diffusion containers by attaching the opening and closing unit 200 to a plurality of container bodies 300 accommodating the aroma diffusion module 100 in which various types of aroma diffusion media 140 are inserted and putting the manufactured aroma diffusion containers in a box (see FIG. 8).

The types and configurations of the aroma media that may be used in the aroma diffusion module 100 are as follows. Examples 1 to 11 to be described below are examples according to kinds of aromas applied to the aroma diffusion medium 140 of the aroma diffusion module 100.

Example 1: Wine Aroma Kit

Types of wine aroma kits may be divided into 1) white wine, 2) red wine, 3) oak aged aroma, and 4) defect aroma. (or smell) of wine to be configured.

The white wine kit may be configured by, containing at least one of orange, lemon, lime, grapefruit, apple, pear, peach, plum, dried plum, pineapple, melon, guava, fashion fruit, lychee, lavender, jasmine, rose, geranium, orange flower, bell pepper, grassy smell, mint, eucalyptus, walnut, almond, hazelnut, and the like.

The red wine aroma kit may be configured by containing at least one of black currant, blackberry, strawberry, raspberry, cherry, dried plum, bell pepper, cigarette, chocolate, vanilla, coffee, pepper, licorice and leather.

The oak aged aroma kit may be configured by containing eugenol, 4-ethylguaiacol, 5-methylfurfural/furfural, cis-oaklactone/trans-oaklactone, vanillia, and the like.

The defect aroma kit of the wine may be configured by containing at least one of vinegar, manicure solvent (acetone), bell pepper, decayed apple, decayed egg, fungus odor, pungent odor, garlic/natural gas odor, smoke odor, bandage odor, and stall odor.

Example 2: Champagne (Sparkling Wine) Aroma Kit

A yeast aroma and a sulfur compound were added to the above-described Example 1, and the rest of the process was the same as in Example 1.

Example 3: Coffee Aroma Kit

A kit may be configured based on a coffee aroma wheel, in which each component that constitutes the aroma of coffee is represented separately.

The coffee aroma kit may be configured by containing at least one of coffee flower, tea rose, caraway, coriander seed, lemon, apple, apricot, blackberry, onion, garlic, cucumber, garden peanut, roasted peanut, walnut, balsamic rice, toast, roasted hazelnut, roasted almond, honey, maple syrup, baker, dark chocolate, Swiss vanilla chocolate, pine, black currant, mint, cinnamon, juniper, pepper, clove, time, tare, pipe tobacco, burnt odor, and charcoal odor.

Example 4: Beer Aroma Kit

A kit is configured by containing a good aroma, odor, or the like of the beer.

The beer aroma kit may be configured by containing at least one of acetaldehyde, acetic acid, almond, hoppy, butyric acid, caprylic acid, sour/buttery, dimethyl sulfide, diacetyl, earthy, ethyl acetate, ethyl hexanoate, geraniol, grainy, hefeweizen (spicy/banana), indole, isoamyl acetate, isovaleric acid, lactic acid, light-Struck, mercaptan (Ethanthiol), metallic(Ferrous sulfate), papery (trans-2-Nonenal), spicy (Eugenol), vanilla, citrus, exotic, linalool, herbal (Myrcene), berry to (b-Ionone), perfume (Citronellol), piney (a-Terpeniol), woody (Caryophyllene/Humulele), grapefruit, apricot, floral, catty, tobacco, furaneol, potato skins, cinnamon, nonanal, anise, and musty.

Example 5: Tea Aroma Kit

The tea aroma kit may be configured by containing at least one of Fresh cut grass, Hay, Spinach, Bean Sprout, Peas, Green Bean, Basil, Parsley, Mint, Thyme, Jasmine, Rose, Honeysuckle, Fresh Butter, Roasted Nut, Malt, Honey, Caramel, Toffe, Vanilla, Toast, Smoke, Tobacco, Leather, Cinnamon, Pepper, Clove, Licorice, Ginger, Pineapple, Banana, Melon, Mango, Apple, Apricot, Pear, Grape, Orange, Lemon, Lime, Raspberry, Strawberry, Musty, Wet Leaves, Pine, Wet Wood, Cedar, Oak, and Eucalypt.

Example 6: Sake Aroma

The sake aroma kit may be configured by containing at least one of Ginjyo (floral), Cedar, Grassy, Nutty, Spicy, Cereal (Koji), Sweet, Caramel, Burnt, Oxidized (stale), Sulfury, Contaminated, Diacetyl, Fatty, and Acetic.

Example 7: Aroma Kit for Improving Children's Cognitive Ability

An aroma kit for improving children's cognitive ability may be configured by containing at least one of 1) Peppermint, 2) Rosemary, 3) Spearmint, 4) Jasmine, 5) Rose, 6) Ginger, 7) Lemon, 8) Grapefruit, 9) Thyme, 10) coriander, and 11) Black Pepper.

Example 8: Aroma Kit for Improving Aged Cognitive Ability

An aroma kit for improving aged cognitive ability may be configured by containing at least one of 1) Rose, 2) Cherry, 3) Smoke, 4) Peppermint, 5) Leather, 6) Lilac, 7) Pineapple, 8) to Soap, 9) Strawberry, 10) Natural Gas, 11) Lemon, and 12) Clove.

Example 9: Ice Cream Aroma Kit

The ice cream aroma kit may be configured by containing at least one of 1) Banana Nut Fudge, 2) Black Walnut, 3)

Burgundy Cherry, 4) Butterscotch, 5) Ribbon, 6) Cherry Macaroon, 7) Chocolate, 8) Chocolate Almond, 9) Chocolate Chip, 10) Chocolate Fudge, 11) Chocolate Mint, 12) Chocolate, 13) Ribbon, 14) Coffee, 15) Coffee Candy, 16) Date Nut, 17) Egg Nog, 18) French Vanilla, 19) Green Mint Stick, 20) Lemon Crisp, 21) Lemon Custard, 22) Lemon Sherbet, 23) Maple Nut, 24) Orange Sherbet, 25) Peach, 26) Peppermint Fudge Ribbon, 27) Peppermint Stick, 28) Pineapple Sherbet, 29) Raspberry Sherbet, 30) Rocky Road, 31) Strawberry, 32) Vanilla, and 33) Vanilla Burnt Almond.

Example 10: Jelly Belly Aroma Kit

The jelly belly aroma kit may be configured by containing at least one of 1) Toasted Marshmallow, 2) Island Punch, 3) Strawberry Daiquiri, 4) Blueberry, 5) Coconut, 6) Raspberry, 7) Crushed Pineapple, 8) Cream Soda, 9) Tangerine, 10) Grape, 11) Pina Colada, 12) Lemon Lime, 13) Lemon, 14) Peach, 15) Tutti-Frutti, 16) Mango, 17) Berry Blue, 18) Wateermelon, 19) Lemon Drop, 20) Strawberry Jam, 21) Top Banana, 22) Cafe Latte, 23) Strawberry Cheesecake, 24) cherry Cola, 25) Orange Sherbet, 26) Very cherry, 27) Bubble Gum, 28) Green Apple, 29) Cappuccino, 30) cotton Candy, 31) Chocolate Pudding, 32) Caramel Apple, 33) Kiwi, 34) Vanilla, 35) Orange, 36) Plum, 37) Dark chocolate, 38) Wild Blackberry, 39) Pomegranate, 40) Pink Grapefruit, 41) Red Apple, 42) Margarite, 43) Caramel Corn, 44) Cantaloupe, 45) Green Tea, 46) Buttered Popcorn, 47) Juicy Pear, 48) Sizzling Cinnamon, 49) Cinnamon, and 50) Licorice.

Example 11: Perfume Aroma

The perfume aroma kit may be configured by containing components configuring the perfume.
100: fragrance emission module
110: second hollow
120: module body
130: first hollow
140: aroma diffusion medium
150: plug
200: opening and closing unit
210: One-touch cap
211: connection portion
220: sniffing port
230: valve unit
231: base portion
232: extension portion
233: membrane member
235: slit
240: protrusion
300: container body
310: head portion
320: body portion
330: bottom portion
P: pipette
MF: Membrane filter

The invention claimed is:

1. An aroma diffusion container comprising:
a container body;
an opening and closing unit coupled to the upper end of the container body; and
an aroma diffusion module mounted in the container body, wherein the aroma diffusion module includes
a porous module body;
a first hollow formed at one side of the module body; and
a second hollow formed inside the module body, a porous aroma diffusion medium is accommodated in the first hollow, and
the second hollow allows external air to be introduced into the container body through a slit of a membrane member unit.

2. The aroma diffusion container of claim 1, wherein the first hollow is in contact with the inner side of a bottom portion of the container body, and the second hollow is adjacent to a head portion formed on the upper end of the container body.

3. The aroma diffusion container of claim 2, wherein the aroma diffusion module has a column shape extending from the head portion of the container body to the bottom portion of the container body.

4. The aroma diffusion container of claim 1, wherein the container body is made of a flexible material.

5. The aroma diffusion container of claim 4, wherein the container body has a multilayered structure in which a nylon layer is formed between resin layers formed of the flexible material.

6. The aroma diffusion container of claim 4, wherein the flexible material is low density polyethylene (LDPE) or high density polyethylene (HDPE).

7. The aroma diffusion container of claim 1, wherein an antioxidant and a deoxidizer are contained in the aroma diffusion module.

8. The aroma diffusion container of claim 7, wherein the antioxidant includes at least one of butylated hydroxy aisole (BHA), butylated hydroxy toluene (BHT), tert-butylhydroxyquinone (TBHQ), ethylenediaminetetraacetic acid (EDTA), phenolic acids, and polyphenols.

9. The aroma diffusion container of claim 1, wherein the opening and closing unit includes a valve member having the membrane member unit made of a flexible material, and the membrane member unit is convexed in upward direction.

10. The aroma diffusion container of claim 1, wherein the opening and closing unit includes a sniffing port which is coupled to the container body and gradually expanded in upward direction.

11. The aroma diffusion container of claim 1, wherein a liquid aroma component is absorbed in the porous aroma diffusion medium.

12. The aroma diffusion container of claim 1, wherein the container body is sealed and wherein, in the container body, an aroma component volatilized to a gaseous state from a liquid aroma component absorbed in the porous aroma diffusion medium is present at a predetermined concentration.

13. The aroma diffusion container of claim 1, wherein the airtightness of an aroma component in a gaseous state present inside the container body is maintained by a multiple sealed structure formed by an edge of a one-touch cap, a protrusion formed on an inner surface of the one-touch cap, or the membrane member unit.

14. The aroma diffusion container of claim 1, wherein an aroma component in a gaseous state is present inside the container body;
wherein the opening and closing unit includes a sniffing port and a one-touch cap, the opening and closing unit allowing the aroma component to be discharged through the sniffing port if the one-touch cap is open; and
wherein a deoxidizer and an antioxidant are contained in the aroma diffusion module.

15. An aroma diffusion kit comprising:
multiple aroma diffusion containers, wherein at least one of the multiple aroma diffusion containers is an aroma diffusion container of claim 1, and
aroma diffusion media, wherein the aroma diffusion media of each of the multiple aroma diffusion containers includes a different aroma material.

* * * * *